(12) United States Patent
Winkelman et al.

(10) Patent No.: US 9,176,121 B2
(45) Date of Patent: Nov. 3, 2015

(54) IDENTIFICATION OF BLOOD ELEMENTS USING INVERTED MICROSCOPY

(75) Inventors: James W. Winkelman, Chestnut Hill, MA (US); Milenko J. Tanasijevic, West Newton, MA (US); David Zahniser, Wellesley, MA (US)

(73) Assignee: Roche Diagnostics Hematology, Inc., Westborough, MA (US)

( * ) Notice: Subject to any disclaimer, the term of this patent is extended or adjusted under 35 U.S.C. 154(b) by 416 days.

(21) Appl. No.: 11/057,095

(22) Filed: Feb. 11, 2005

(65) Prior Publication Data

US 2008/0138852 A1   Jun. 12, 2008

Related U.S. Application Data

(60) Provisional application No. 60/544,377, filed on Feb. 13, 2004.

(51) Int. Cl.
*G01N 33/50* (2006.01)
*G01N 15/00* (2006.01)
*G01N 15/14* (2006.01)

(52) U.S. Cl.
CPC ...... *G01N 33/5094* (2013.01); *G01N 2015/008* (2013.01); *G01N 2015/0073* (2013.01); *G01N 2015/0084* (2013.01); *G01N 2015/144* (2013.01); *G01N 2015/1486* (2013.01); *G01N 2015/1497* (2013.01)

(58) Field of Classification Search
CPC .................. G01N 33/5094; G01N 2015/0073; G06K 9/00127
USPC ..................................................... 356/39–42
See application file for complete search history.

(56) References Cited

U.S. PATENT DOCUMENTS

| | | | | |
|---|---|---|---|---|
| 3,437,395 A | * | 4/1969 | Rosenberger et al. | 359/363 |
| 3,454,337 A | * | 7/1969 | Wein et al. | 356/36 |
| 3,503,684 A | * | 3/1970 | Norgren et al. | 356/39 |
| 3,770,349 A | * | 11/1973 | Legorreta-Sanchez | 356/73 |
| 3,888,206 A | * | 6/1975 | Faulkner | 118/100 |

(Continued)

FOREIGN PATENT DOCUMENTS

| | | |
|---|---|---|
| JP | 63-073149 | 4/1988 |
| JP | 07-020650 | 1/1995 |

(Continued)

OTHER PUBLICATIONS

Sanders et al. "A High Yield Technique for Preparing Cells Fixed in Suspension for Scanning Electron Microscopy", The Journal of Cell Biology, vol. 67, 1975, pp. 476-480.*

(Continued)

*Primary Examiner* — Gregory J Toatley, Jr.
*Assistant Examiner* — Rebecca C Bryant
(74) *Attorney, Agent, or Firm* — Fish & Richardson P.C.

(57) ABSTRACT

A method of identifying the elements of a blood sample including placing an aliquot of blood on a transparent substrate such as a coverslip. The blood is allowed to stand and the cells to settle to form a layer or matrix. Inverted microscopy is used to identify the elements in the sample. Various forms of illumination may be used alone or in multiple combinations. The method improves the accuracy due to homogenous distribution of formed elements in the wet drop or aliquot, simplifies the method, lowers the cost of the test and results in a shortened analytical cycle time.

25 Claims, 6 Drawing Sheets

(56) References Cited

U.S. PATENT DOCUMENTS

| | | | | |
|---|---|---|---|---|
| 3,916,205 | A * | 10/1975 | Kleinerman | 250/461.2 |
| 3,997,838 | A * | 12/1976 | Shamos et al. | 324/71.1 |
| 4,125,828 | A * | 11/1978 | Resnick et al. | 382/134 |
| 4,207,554 | A * | 6/1980 | Resnick et al. | 382/133 |
| 4,596,035 | A * | 6/1986 | Gershman et al. | 382/134 |
| 4,891,364 | A * | 1/1990 | Kubodera et al. | 514/167 |
| 5,114,350 | A * | 5/1992 | Hewett | 435/286.4 |
| 5,378,633 | A * | 1/1995 | von Behrens et al. | 436/63 |
| 5,407,794 | A | 4/1995 | Kass | |
| 5,578,709 | A | 11/1996 | Woiszwillo | |
| 5,585,246 | A * | 12/1996 | Dubrow et al. | 436/536 |
| 5,742,380 | A * | 4/1998 | Ronn | 356/39 |
| 5,948,686 | A | 9/1999 | Wardlaw | |
| 6,055,060 | A * | 4/2000 | Bolduan et al. | 356/433 |
| 6,151,405 | A | 11/2000 | Douglass et al. | |
| 6,201,607 | B1 * | 3/2001 | Roth et al. | 356/445 |
| 6,235,536 | B1 | 5/2001 | Wardlaw | |
| 6,249,344 | B1 | 6/2001 | Virag | |
| 6,251,615 | B1 * | 6/2001 | Oberhardt | 435/7.21 |
| 6,350,613 | B1 | 2/2002 | Wardlaw et al. | |
| 6,819,484 | B2 * | 11/2004 | Aono et al. | 359/368 |
| 6,869,570 | B2 | 3/2005 | Wardlaw | |
| 7,270,801 | B2 * | 9/2007 | Weber et al. | 424/9.2 |
| 2002/0041371 | A1 * | 4/2002 | Shepherd et al. | 356/39 |
| 2002/0055178 | A1 | 5/2002 | Wardlaw | |
| 2002/0061602 | A1 * | 5/2002 | Buechler et al. | 436/536 |
| 2002/0077536 | A1 * | 6/2002 | Diab et al. | 600/323 |
| 2002/0122168 | A1 * | 9/2002 | Garcia-Rubio et al. | 356/39 |
| 2002/0167668 | A1 * | 11/2002 | Voelkel | 356/446 |
| 2004/0029213 | A1 * | 2/2004 | Callahan et al. | 435/40.5 |
| 2004/0058311 | A1 * | 3/2004 | Fletcher et al. | 435/4 |
| 2004/0156037 | A1 * | 8/2004 | Mawhirt et al. | 356/39 |
| 2006/0276411 | A1 * | 12/2006 | Simard et al. | 514/23 |
| 2007/0248976 | A1 * | 10/2007 | Harding | 435/6 |

FOREIGN PATENT DOCUMENTS

| | | |
|---|---|---|
| JP | H08-507806 | 8/1996 |
| JP | 09-033411 | 2/1997 |
| JP | 2009-033411 | 2/1997 |
| JP | 09-089774 | 4/1997 |
| JP | 10-185803 | 7/1998 |
| JP | H10-185803 | 7/1998 |
| JP | 11-326208 | 11/1999 |
| JP | H 11-515095 | 12/1999 |
| JP | 2000-500573 | 1/2000 |
| JP | 2005-00573 | 1/2000 |
| JP | 2000500573 | 1/2000 |
| JP | 2001-174456 | 6/2001 |
| JP | 2001-518186 | 10/2001 |
| JP | 2002-516982 | 6/2002 |
| JP | 2002516982 | 6/2002 |
| WO | 94/20856 | 9/1994 |
| WO | WO 97/09616 | 3/1997 |
| WO | WO 98/44333 | 10/1998 |

OTHER PUBLICATIONS

M. Joan Dunlop et al., "Kinetics of Adhesive Interaction In-Vitro of Human Erythrocytes in Plasma," Microvascular Research, 28(1): 62-74 (1984).

H. M. Aus et al., "Bone Marrow Cell Scene Segmentation by Computer-Aided Color Cytophotometry," The Journal of Histochemistry and Cytochemistry, vol. 25, No. 7, pp. 662-667 (1977).

James E. Green, "A Practical Application of Computer Pattern Recognition Research the Abbott ADC-500 Differential Classifier," The Journal of Histochemistry and Cytochemistry, vol. 27, No. 1, pp. 160-173 (1979).

John F. Brenner et al., "An Automated Microscope for Cytologic Research a Preliminary Evaluation," The Journal of Histochemistry and Cytochemistry, vol. 24, No. 1, pp. 100-111 (1976).

Judith L. Larosa and James D. Cawley, Fractal Dimension of Alumina Aggregates Grown in Two Dimensions, Journal of the American Ceramic Society, vol. 75, No. 7, Jul. 1992.

Rogers, C., "Blood Sample Preparation for Automated Differential Systems," American Journal of Medical Technology, 39(11):435-442 (1973).

Dunlop et al., "Kinetics of Adhesive Interaction In-Vitro of Human Erythrocytes in Plasma," Microvascular Research 28(1): 62-74 (1984).

International Search Report for PCT Application No. PCT/US2005/004597, dated Jun. 27, 2005.

Written Opinion of the International Searching Authority for PCT Application No. PCT/US2005/004597.

International Preliminary Report on Patentability for PCT Application No. PCT/US2005/004597, dated Aug. 14, 2006.

Translation of Notice of Allowance issued in Japanese application No. 2010-118064, drafted on Jun. 13, 2012.

De Bault, L.E., "Evaluation of a Cytocentrifuge Technique Effects on Quantitative Determination of Feulgen-Deoxyribonucleic Acid and Total Dry Mass of Human Leukemic Cells," Journal of Histochemisty and Cytochemistry 20(9), pp. 703-709 (1972).

Simmons, Arthur, "Erythrocytes," Technical Hematology (J.B. Lippincott, 1980), pp. 48-52.

Koss, Leopold G., Diagnostic Cytology and Its Histopathologic Bases, vol. 2 (J.B. Lippincott, 1992, 4th Ed.), pp. 1463-1469.

LaRosa et al., "Fractal Dimension of Alumina Aggregates Grown in Two Dimensions," Journal of the American Ceramic Society 75(7), pp. 1981-1984 (1992).

McClatchey, Kenneth D. (ed.), Clinical Laboratory Medicine (Williams & Wilkins, 1994), p. 1723.

StatSpin, CytoFuge 2 Cytocentrifuge System Operator's Manual, 1998.

Collarini et al., "A novel method for depositing erythroid cells onto glass slides for fetal cell analysis," Cytometry 45(4), pp. 304-309 (2001).

Seiter, C., et al., "Contact Angles: New Methods and Measurements", American Laboratory, p. 26 (Feb. 2002).

National Clinical Target Validation Laboratory, Standard Operating Procedures (SOP)for the Preparation of Cytospin Slides of Peripheral Blood Mononuclear Cells (PBMCs)Isolated from Venous Blood, 2006.

Hanes, Heidi, "Cytomorphology Smears for Body Fluids Cytospin Method," 2009, downloaded from internet address http://www.docstoc.com/docs/90095311/Cytomorphology-smears-for-body-fluids.

"Csf Information and Courses from MediaLab, Inc.," document downloaded from internet address http://www.medialabinc.net/csf-keyword.aspx on Feb. 24, 2012.

"Shandon Cytospin 4 Cytocentrifuge," document downloaded from internet address https://www.harlowscientific.com/userfiles/file/Equipment%20Brochures/Thermo%20Shandon%20Cytospin%204%20cytofuge%20clinical%20centrifuge%20brochure%20harlowscientific.pdf on Feb. 24, 2012.

Translation of Office Action in JP Patent Application No. 2006-553311, dated Feb. 28, 2009.

Translation of Office Action in JP Patent Application No. 2006-553311, dated Oct. 24, 2009.

Translation of Office Action in JP Patent Application No. 2006-553311, dated Jul. 6, 2010.

Translation of Office Action in JP Patent Application No. 2010-118604, dated Apr. 19, 2011.

Translation of Office Action in JP Patent Application No. 2010-118604, dated Nov. 29, 2011.

Bacus, J. et al., "Image Processing for Automated Erythrocyte Classification", The Journal of Histochemistry and Cytochemistry, 24: 195-201 (1976).

Bacus, J. et al., "An Automated Method of Differential Red Blood Cell Classification with Application to the Diagnosis of Anemia", The Journal of Histochemistry and Cytochemistry 25: 614-32 (1977).

Bacus, J., "Quantitative Morphological Analysis of Red Blood Cells," Blood Cells 6: 295-314 (1980).

Bacus, J., "Digital Image Processing Measurements of Red Blood Cell Size and Hemoglobin Content," Advances in Hematological Methods: The Blood Count, Ch. 14, pp. 157-81 (1982).

Bacus, J., "Quantitative Red Cell Morphology," Monogr. Clin. Cytol. 9: 1-27 (1984).

Bacus, J., "Cytometric approaches to red blood cells," Pure & Appl. Chem. 57: 593-98 (1985).

* cited by examiner

IDENTIFICATION OF BLOOD ELEMENTS USING INVERTED MICROSCOPY

PRIORITY INFORMATION

This application claims priority to U.S. Patent Appln. Ser. No. 60/544,377, filed on Feb. 13, 2004 which is incorporated herein in its entirety.

BACKGROUND OF THE INVENTION

1. Field of the Invention

This invention relates to method and apparatus for analyzing whole blood samples, and to methods and apparatus for evaluating constituents within a whole blood sample such as red blood cells, white blood cells, platelets, etc.

2. Description of the Prior Art

Physicians often utilize a blood test to determine the health of a patient. The complete Blood Count (CBC) is the most commonly performed clinical laboratory test in the United States and the world. Rapid identification and enumeration of the various components of biological fluids is an important diagnostic aim Minimal processing and handling of samples would contribute to the widespread use of such techniques.

Historically, a blood sample is taken from a patient and then sent to a laboratory for evaluation. Current CBC methods and instruments are highly evolved, using multi-channel, multi-detector flow system based technology. CBC instruments aspirate anticoagulated whole blood and divide it into several analysis streams to perform the different elements of the CBC. The elements include red blood cell count (RBC), hemoglobin (Hb), hematocrit (Hct) indices (MCV, MCH, MCHC), and red cell morphology; white blood cell count (WBC) and WBC differential count (enumeration of the different normal and abnormal white blood cell types; and platelet count.

The most common tests performed on blood samples taken from patients are the hematocrit (Hct), or the hemoglobin (Hb), which are often used interchangeably, depending upon the individual preference of the treating physician. They are used to determine anemia, to monitor conditions in which the blood loss occurs, chronic diseases, drug reactions, allergies, and the course of therapy.

The Hct of a sample of blood is defined as the ratio of the volume of erythrocytes (red blood cells) to that of the whole blood. It is expressed as a percentage or, preferably, as a decimal fraction. The units (L/L) are implied. The venous hematocrit agrees closely with the hematocrit obtained from a skin puncture; both are greater than the total body hematocrit.

The Hct and Hb are often provided along with the total red blood cell count (RBC) which is usually expressed in the form of a concentration—cells per unit volume of blood. Once these three values are known (Hct, Hb and RBC), three red blood cell indices are calculated. These indices are particularly useful in the morphologic characterization of anemias. These values include the mean cell volume (MCV) which is the average volume of red blood cells and is calculated from the Hct and the RBC. Utilizing the formula:

MCV=Hct×1,000/RBC(in millions per μl)

The mean cell hemoglobin (MCH) may also be calculated and is the content of Hb in the average red blood cell; it is calculated from the Hb concentration and the RBC utilizing the following formula:

$$MCH = \frac{Hb(\text{in g per liter})}{RBC(\text{in millions per } \mu l)}$$

Another index calculable from the Hb and Hct is the mean cell hemoglobin concentration (MCHC). This index is the average concentration of Hb in a given volume of packed red blood cells. It is calculated using the following formula:

$$MCHC = \frac{Hb(\text{in g/dl})}{Hct}$$

Other characteristics of red blood cells which are available utilizing today's testing methods include values for the variability of the MCV about a mean value and estimates of abnormality in red blood cell morphology.

The above described indices are discussed in much greater detail in John Bernard Henry, M.D., Clinical Diagnosis And Management By Laboratory Methods, Part IV (17th edition 1984).

Modern clinical laboratory instrumentation has been built to make these primary analyses simultaneously in vitro on blood samples removed from the patient and the calculated indices are readily produced by these instruments. The calculated indices are often the preferred data on which physicians base their conclusions about a patient's condition.

A large number of testing methods, instrumentation, and techniques have been used in measuring and approximating values for Hct, Hb and RBC. The most common method used to determine the Hct (the ratio of packed red blood cells to volume of whole blood) involves centrifugation wherein a given blood sample is placed into a centrifuge for five minutes at approximately 10,000 to 12,000 g. The volume is then calculated by measuring the level of the red blood cells as a ratio of the total volume.

Methods used in the art to determine the Hb in a sample of blood include the cyanmethemoglobin method, the oxyhemoglobin method and the method of measuring iron content of the sample. Of the above three methods, the first (the cyanmethoglobin method) is recommended by the International Committee for Standardization in Hematology. That method involves diluting a sample of blood in a solution of potassium ferricyanide and potassium cyanide. The potassium ferricyanide oxidizes hemoglobins and potassium cyanide provides cyanide ions to form hemiglobincyanide which has a broad absorption maximum at a wavelength of approximately 540 nm. The absorbance of the overall solution can then be measured in a photometer or spectrophotometer at 540 nm and compared with that of a standard hemoglobincyanide solution.

A large number of testing methods techniques and instruments have also been used in measurement of WBC counts, WBC differential counts and platelet counts. Rather than attempting to review the entire filed, refer to Henry (Ibid.)

Fully automated blood analysis systems are usually flow based and can cost more that $300,000. The systems require extensive calibration and control, maintenance, skilled operators and they have substantial costs associated with reagents, consumables and disposables. A large proportion of blood specimens processed by the systems requires further testing, depending of the laboratory policy regarding "flagging" criteria for certain findings and typically is from 10 to 50% of the samples. Retesting most frequently is required for direct visualization by a technologist, of abnormal RBC morphology or of the WBC differential due to an abnormal distribution of cell types or cells whose origin could be from hematologic or other malignancies or viral diseases. The additional testing includes retrieving the blood tube, removing blood from the tube and preparing and staining a smear on a glass slide, followed by visualization and analysis of the cells by a skilled technologist. The follow-up tests costs up to three times that of the initial instrumental analysis.

For follow-up, the sample is evaluated by smearing a small amount of blood on a slide, drying, fixing and staining it and then examination of the smear under a microscope. Unfortunately, the accuracy and reliability of the results depends largely on the technician's experience and technique. Additionally, blood smears are labor intensive and costly. Although the preparation and staining can be automated, examination remains a manual task.

A known reference method for evaluating a whole blood sample involves diluting a volume of whole blood, placing it within a "counting chamber", and manually evaluating the constituent cells within the diluted sample. Dilution is necessary because the number and concentration of the red blood cells (RBCs) in whole blood vastly outnumber other constituent cells. To determine a WBC count, the whole blood sample must be diluted within a range of about one part blood to twenty parts diluent (1:20) up to a dilution of approximately 1:256, depending upon the exact technique used, and it is also generally necessary to selectively lyse the RBCs with one or more reagents. Lysing the RBCs effectively removes them from view so that the WBCs can be seen. To determine a platelet count, the blood sample must be diluted within a range of about 1:100 to approximately 1:50,000. Platelet counts do not, however, require a lysis of the RBCs in the sample. A disadvantage of this method of evaluating a whole blood sample is that the dilution process is time consuming and expensive. In addition, adding diluents to the whole blood sample increases the error probability within the sample data.

A modern method for evaluating a blood sample is impedance or optical flow cytometry. Flow cytometry involves circulating a diluted blood sample through one or more small diameter orifices, some with reagent addition streams flowing into them, each adjacent to an impedance type or an optical type sensor which evaluates the constituent cells as they pass through the orifice in single file. Different constituents may require different flow streams for their detection and estimation. For example, the blood sample must be diluted to mitigate the overwhelming number of the RBCs relative to the WBCs and the platelets for counting of each of these constituents. Further, separate streams of flow may be required for differentiation of white blood cells in order to do WBC differential counts. Each such stream imposes requirements for stream separation by valves or other means, pumps and detection devices. There are many variations of such processes in different flow based CBC instruments but all add complexity, numbers of moving parts, opportunities for component failure, needs for maintenance and costs. In addition, fluidics are required for different reagents to be added to different streams. Although more expedient and consistent than the above described reference methods, flow cytometry also possesses numerous disadvantages. Some of those disadvantages stem from the plumbing required to carry the sample to, and the fluid controls necessary to control the fluid flow rate through, the sensor means. The precise control of the sample flow is essential to the operation of the flow cytometer. The plumbing within flow cytometers may leak, potentially compromising the accuracy and the safety of the equipment. The fluid flow controls and dilution equipment, on the other hand, require periodic recalibration. The need for recalibration illustrates the potential for inaccurate results and the undesirable operating costs that exist with many presently available hematology analyzers which use flow cytometers. Another disadvantage is the volume of reagents required. Because of the large dilution ratios employed, correspondingly large volumes of liquid reagents are necessary. The large reagent volume increases the cost of the testing and creates a waste disposal problem.

Another approach to cellular analysis is volumetric capillary scanning as outlined in U.S. Pat. Nos. 5,547,849 and 5,585,246 for example, wherein a relatively undiluted sample of whole blood is placed into a capillary of known volume and thickness and is examined while the blood is in a quiescent state. This technique deals with the presence of the RBCs by limiting the scanning wavelengths to those with which the RBCs appear relatively transparent, and it requires that the sample be treated so that the RBCs do not aggregate during the measurement process. Thus, this technique is limited to the use of longer wavelength fluorescence, and there is no provision for the examination of RBCs and platelets or the examination of any cellular morphology.

U.S. Pat. No. 5,948,686 describes a method and apparatus for use in examining and obtaining information from a quiescent substantially undiluted anti-coagulated whole blood sample which is contained in a chamber having a top and bottom. Generally, the only reagents used were dyes, stains and anticoagulants, and these reagents were not added for the purpose of diluting the sample but rather were added to produce a reaction, an effect, or the like that facilitates the test at hand.

According to the invention, a method for evaluating constituents in undiluted anti-coagulated whole blood included the steps of: a) providing a sample chamber; b) admixing a sensible colorant with the sample of whole blood; c) inserting the admixed sample into the sample chamber; d) quiescently holding the admixed sample within the chamber until rouleaux and lacunae form within the sample; and e) evaluating a target constituent disposed within the lacunae.

SUMMARY OF THE INVENTION

The invention is directed to an improved method of identifying the elements of a blood sample. The method includes placing an aliquot of blood on a substrate such as a coverslip or another transparent support or platform. The blood is allowed to stand and cells to settle to form a layer or matrix and then using inverted microscopy to identify the elements in the sample. Various forms of illumination may be used alone or in multiple combinations. The method improves the accuracy due to homogenous distribution of formed elements in the wet drop or aliquot, simplifies the method, lowers the cost of the test and results in a shortened analytical cycle time.

An object of the present invention is to provide an improved method for identifying the elements in a blood sample using inverted microscopy.

It is a further object of the invention to use a darkfield (epi-illuminated) reflectance inverted microscopy by itself or in combination with angled brightfield or other systems of direct transmission illumination.

It is an object of this invention to provide lower cost instrumentation, which provides all the main parameters of the CBC and the WBC differential.

It is another object of the present invention to provide instrumentation, which lowers consumable and reagent costs, along with greater throughput, and less follow-up testing which in return requires less operator time and skill.

DESCRIPTION OF THE DRAWINGS

Other objects, features and advantages of the present invention will become more apparent as the description proceeds with reference to the accompanying drawings, wherein:

FIG. 6A-D are photographs of blood samples illustrating a time sequence;

DETAILED DESCRIPTION OF THE INVENTION

Generally, the invention includes a new straightforward method of preparing a whole blood sample, in which a homogeneous monolayer distribution of RBCs, WBCs, and platelets is obtained from an aliquot of blood. Basically, an aliquot of anticoagulated blood is diluted with a stain reagent or other diluent and the diluted aliquot is placed onto a transparent substrate such as a coverslip, which may be glass or plastic. A droplet forms naturally, but may be constrained by external forces. Within seconds, cells settle to the surface of the coverslip. The cells do not overlap, but form a layer which can be easily viewed on an inverted microscope. The microscopic appearance of these preparations is similar to that of a well-prepared "smear" for a manual WBC differential count. The drop method described herein should have an advantage over the "smear" in that a homogeneous distribution of the cells is visible as opposed to selective distribution of some cells at the feather edge and lateral margins of glass slide "wedge" preparations. Also the morphology of the white cells and red cells is not altered as it can be in a smearing process which leaves flattened and dried cells on the surface of the glass slide. The central pallor and natural shape of the red cells is readily observable as are features of certain white blood cells such as the vibrational motion of their granules, which are never seen in conventional smears.

Figure 1A:
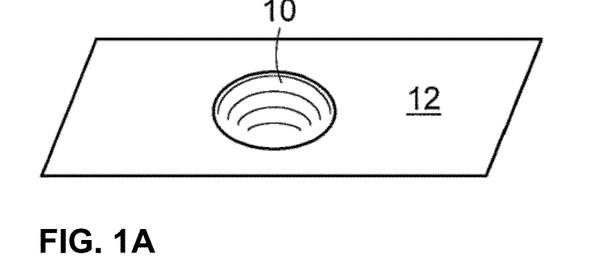
FIGS. 1A-C is a schematic showing of an aliquot of blood on a substrate illustrating a process settling to form a monolayer at the base of the aliquot on the substrate.
Figure 1B:
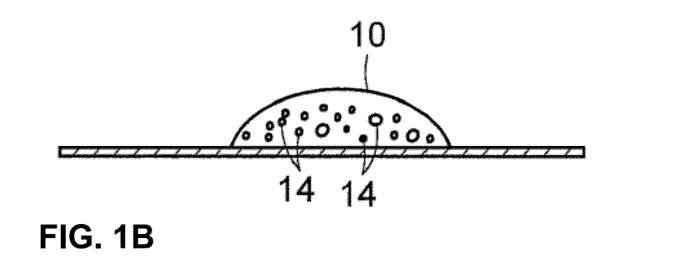
Figure 1C:
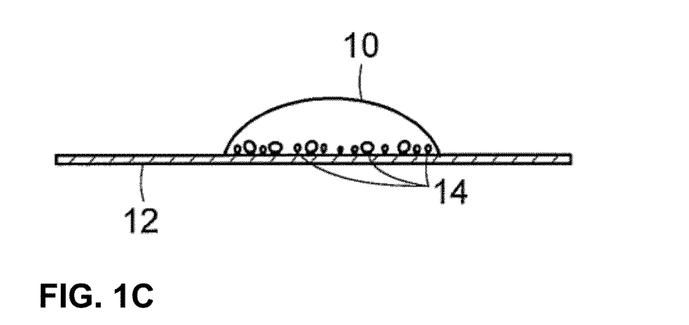

As shown in FIG. 1A-C, an aliquot of blood 10, which may be diluted with stain and/or saline, is placed on a #0 coverslip 12. From the side, the aliquot 10 forms a hemispherical shape. Components 14 of the blood are initially distributed through the aliquot. As time passes the components of the blood 14 settle down onto the surface of the glass coverslip 12.

The invention involves employing inverted darkfield (epi-illuminated) reflectance microspectrophotometry and image analysis to analyze formed elements in various fluids. Other illumination can be employed separately or together with the above. This approach eliminates many of the problems that were intrinsic in the prior art methods including air drying and other steps in slide preparation, or steps in the staining and the viewing of the cells, etc. It further assures the homogeneous distribution of cells, a known deficiency of the conventional smears that adversely affects accuracy. For instance it avoids the irregular distribution of red cells and white cells of different sizes and densities that occur during preparation of an ordinary smear.

More specifically with reference to FIGS. 2-5, "Inverted microscope optics" are used to observe and/or analyze the sample. With this optical system the microscope objective is below the glass substrate supporting the aliquot of the mixture. Objective lenses may vary in magnification power from 4× to 100×. The preferred embodiment would use 20× and/or 50× objectives.

Figure 2:
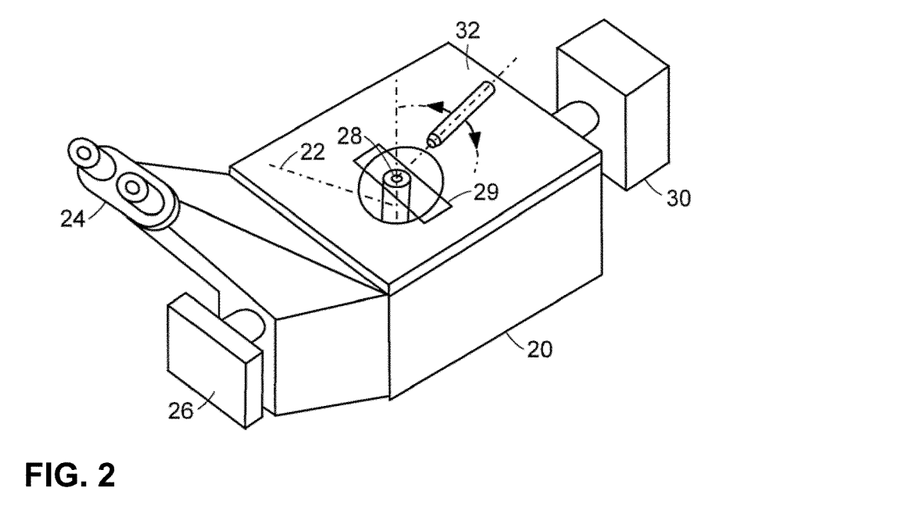
FIG. 2 is a schematic showing a representative an inverted microscope.

An inverted microscope 20 is shown in FIG. 2. By using an inverted microscope 20, the layer(s) formed by the components of the blood can be observed. With an inverted microscope 20, the objective lens 22 and the optical coupling to the eyepieces 24 or camera 26 attachment are below the specimen 28 rather than above the specimen 28 as is typical of most microscopes, and exclusively, those used to examine blood smears as part of the CBC. This is ideal for observing the layer of objects that would have settled onto the glass substrate 29 from the dome shaped aliquot 28 of (diluted) blood. For reflected light 30 the source of illumination is also below the specimen 28, and is projected onto the specimen from underneath using a half-reflecting mirror or other means in the light path below the objective lens 22. Light reflecting from the specimen is passed back through the mirror into the eyepiece or camera. For transmitted light 32 in an inverted microscope 20, the source of illumination is above the specimen. Typically the source of transmitted light 32 is straight above (90 degrees to the glass substrate). However, in this application an angled source of illumination from above provides a "3-D" effect that allows visualization of the components of the blood in a single focal plane. By varying the angle of the illumination, different components can be emphasized and various "3-D" effects are obtained. In addition, vibration of granules within white blood cells has been noted with both reflected and transmitted illumination. In the alternative, one may use a good lens and camera to observe the aliquot.

Figure 3:
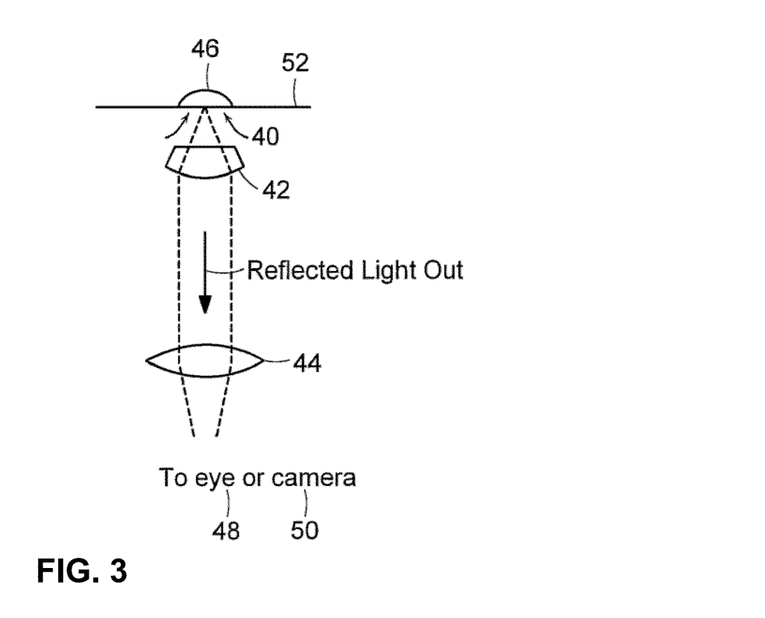
FIG. 3 is a schematic representation of reflected darkfield illumination.
Figure 4:
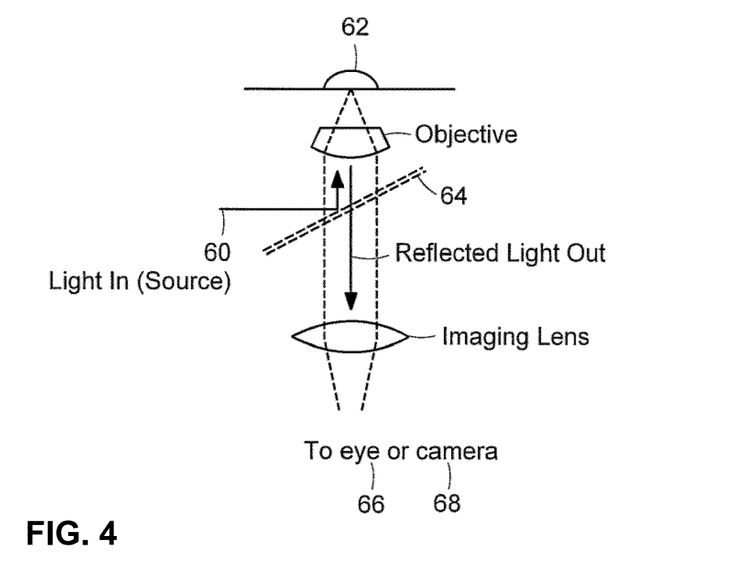
FIG. 4 is a schematic representation of reflected illumination.
Figure 5:
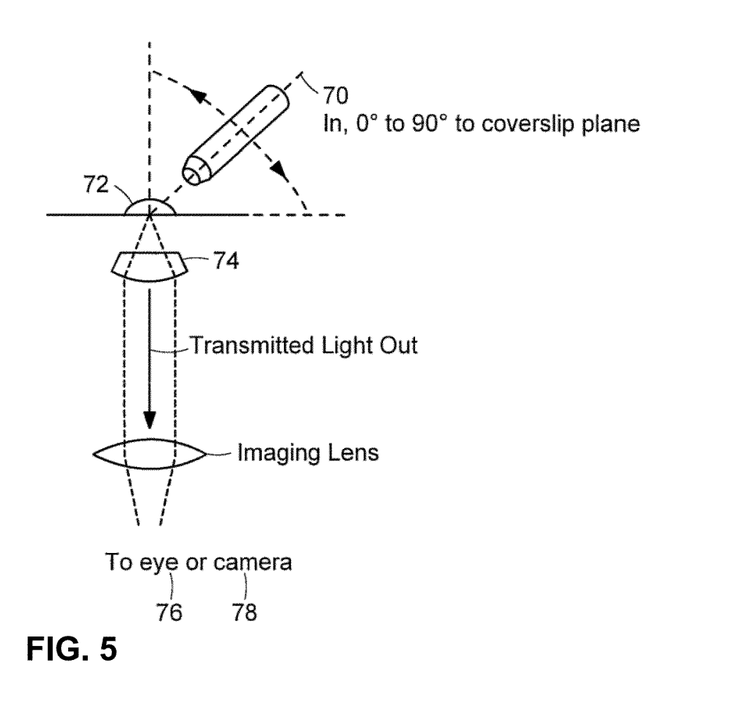
FIG. 5 is a schematic representation of transmitted light, in this illustration.

Several modes of illumination can be used to observe the components of the blood as shown in FIGS. 3-5. Darkfield reflected is used in one mode to observe the bottom layer of cells by illuminating the specimen from below at an angle to the perpendicular to the substrate and collecting reflected light into an objective positioned below and perpendicular to the substrate. Reflected illumination is another mode, observing the bottom layer of cells from below while illuminating the specimen through the same optics as the observation (i.e. using the objective lens as both the source of light and for the collection of reflected light). Still another mode is a transmitted illumination, observing the bottom layer of cells by illuminating the specimen from directly above, while collecting transmitted light coming into the objective directly below. Yet still another mode is transmitted "angled" illumination, observing the bottom layer of cells by illuminating the specimen from above at an angle to the perpendicular to the substrate. Light is collected into the objective positioned perpendicular and below the substrate. Any combination of these modes may be employed simultaneously to provide optimal images of any of the cellular components of blood, and switching between modes can be employed to optimally visualize different components sequentially.

In reflected darkfield illumination as shown in FIG. 3, the light source 40 is projected onto the specimen 46 at an angle from below. This can be projected from outside the objective lens 42, or some special lenses that have an outside collar that will carry the light up around the objective lens and project it at an angle at the tip of the objective. Light hitting the specimen 46 is then reflected straight down into the objective lens 42 and to the eyepieces 48 or the camera 50. Depending upon the angle and the aperture settings of the light source, a harsh image showing only edges or granular objects can be created (hard contrast), or a soft image showing a full spectrum of components of blood can be created (soft contrast). Because reflected illumination is usually used on solid objects, such as with metallurgical applications, the objective lenses 42 are not corrected for use with a transparent substrate 52. For that reason a very thin glass substrate, such as a #0 or #00 coverslip, provides the best quality image.

In reflected illumination as illustrated in FIG. 4, the light source 60 is projected onto the specimen 62 straight on from below. This is accomplished by using a half reflecting mirror 64 to project light from the side, up towards the specimen 62. Light that is reflected from the specimen directly downwards passes through the half mirror 64 and is observed in the eyepieces 66 or the camera 68. Again, contrast can be adjusted to emphasize different types of objects.

When using transmitted light as shown in FIG. 5, the light source 70 is projected downwards above the specimen 72, and the light is collected directly through the objective lens 74 to the eyepieces 76 or the camera 78. If the light source 70 is directly above, the system performs exactly like an upside down standard microscope. For observing the layer(s) of components of blood, an angled source of illumination provides an ability to emphasize different components of the blood, and to generate "3-D" effects such that the cells will appear as three dimensional. In particular the red blood cells appear as 3-D "inflated" objects. Depending on the angle they might have a convex or a concave appearance. Some angles emphasize the white blood cells, whereas other angles emphasize the red blood cells or platelets. Again, contrast can be adjusted to emphasize different types of objects.

There can be various combinations of the illumination modes described above. The optimal illumination condition for observing certain elements of the sample could, for example, consist of both a reflected mode and a transmitted mode turned on simultaneously. The angles of illumination can also be altered as best determined for each type of sample and each dilution. At times, it may be desired to add dispersing agents, colloidal agents, etc.

Experimental Section

Specimen:

An anticoagulated blood specimen (using heparin or EDTA as anticoagulant) was collected from 1) a finger stick or 2) venous blood by phlebotomy into a Becton Dickenson vacutainer (such as BD #8002561).

Specimen Processing:

Before analyzing the specimen, it should be kept at ambient temperature with a gentle rocking action, as with conventional automated CBC instruments. An aliquot was aspirated from the blood sample. The aliquot is preferably 1 drop or about 25 microliters, from a range of 10 microliters to 200 microliters.

Any of the following can then be performed:
1. Use the blood without any dilution.
2. Add an aliquot of a buffer to the blood. Buffer may be 0.9 N Saline at various pH's.
3. Add an aliquot of a mixture of buffer and stain to the blood. Buffer may be 0.9 N Saline and stain may be Wright-Giemsa (Sigma Diagnostics, St. Louis Mo.), which may be in a ratio of 1:1 to 5:1, preferably 2:1 (buffer:stain).
4. Add an aliquot of stain only to the blood. Stain may be Wright-Giemsa (Sigma Diagnostics, St. Louis Mo.).

When mixing aliquots, the volume of blood to buffer/stain may be 1:1 to 1:20 or greater, preferably 1:9 (blood:buffer/stain). The mixture was maintained at room temperature with gentle rocking. When using stain, sufficient time (1-10 minutes) should be allowed for the stain to react with the cells, preferably about 1 minute.

Preparation of Sample on Substrate:

One drop (5 to 100 microliters, preferably 50 microliter) of mixture was transferred to an ultrathin glass substrate (for example a coverslip, No. 0 or No. 00 thickness, 22×40 mm, Erie Scientific, Portsmouth N.H.). A drop was maintained on a slide at constant ambient temperature and humidity. Sufficient time (10 seconds to 2 minutes) was allowed, preferably 30 seconds, for cells to form a layer at the base in which there is very little motion of cells, i.e. very slow addition of new cells to the monolayer, layer or matrix at the base of the drop.

Figure 6A:
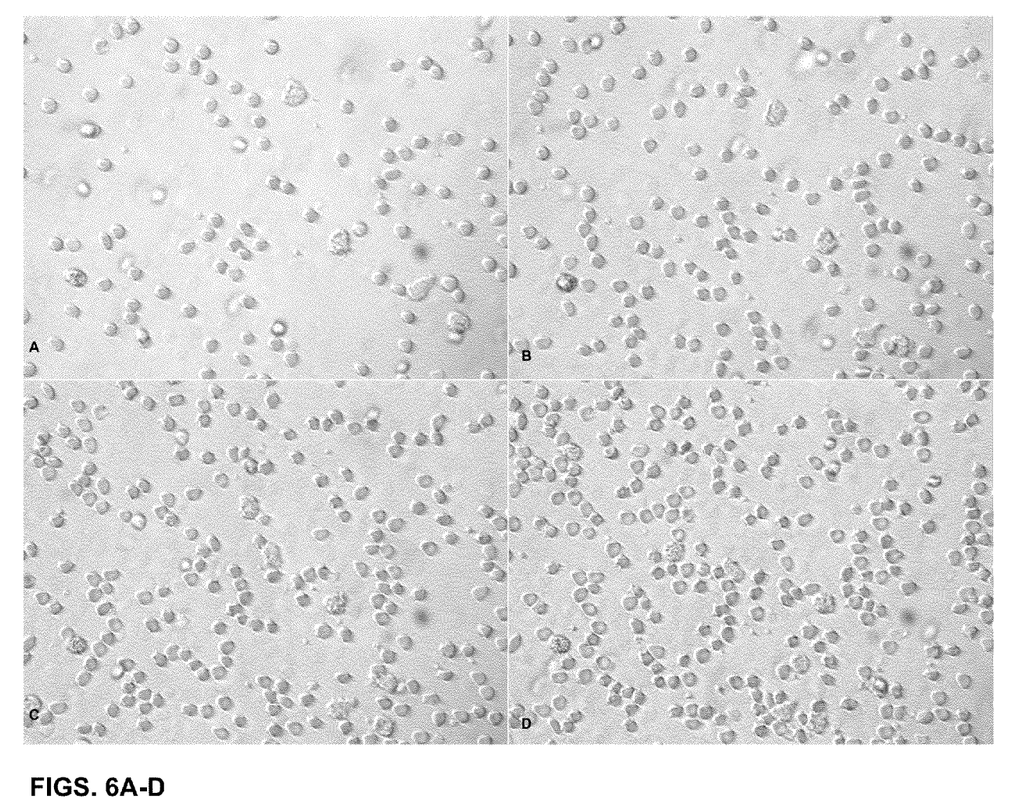
Figure 7:
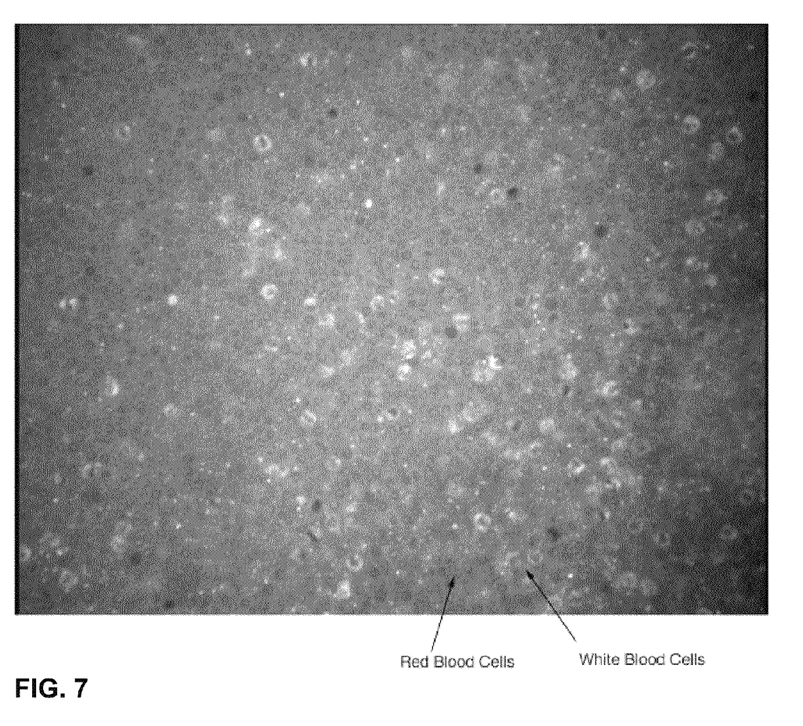
FIG. 7 is a photograph of a blood sample using darkfield reflected mode in combination with angled transmitted illumination.

There is a tradeoff between dilution and time for the formation of a monolayer or layer suitable for cell counting, due to the eventual forming of a confluent layer of cells. Less dilution means that a confluent layer will form more quickly on the bottom. FIGS. 6A-D, are a series of digital images were taken over a period of time. To set up the samples, an aliquot of blood, diluted with saline 1:20 (blood:saline) was placed on a #0 coverslip and observed on an inverted microscope with angled transmitted illumination using white light, at a low angle to the plane of the coverslip. The angle of transmitted illumination provided a convex appearance to the cells. A 50× objective was used. FIG. 6A, was obtained at 30 seconds after mixing and placing the aliquot on the coverslip. As seen there are relatively few cells in the bottom most plane of focus. FIG. 6B was obtained at 120 seconds. There is a substantial increase in the number of cells in the focal plane. FIGS. 6C and D were obtained at 240 and 360 seconds respectively and illustrate still further increases in the number of cells in focus.

These images illustrate the time course in the settling of cells into the plane of focus. The time course will depend on the dilution. There will, for a given dilution, be an optimal time for the counting of the different cell types. In this set of images there is a clear distinction between the red 80 and white blood cells 82.

Using the above techniques and equipment, FIGS. 7-10 were prepared. Specifically, in FIG. 7, an aliquot of blood was mixed 1:1 with stain, and illuminated using the darkfield reflected mode on an inverted microscope in combination with angled transmitted illumination. Within the plane of focus, a single layer shows red blood cells 80 and white blood cells 82 that are clearly distinguishable. The white cells are well stained. A 20× objective was used.

Figure 8:
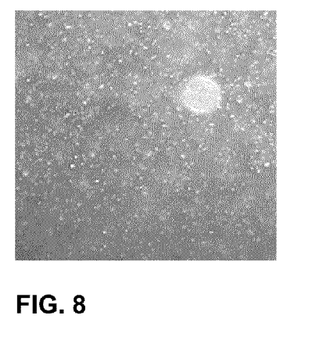
FIG. 8 is a photograph of a platelets using a darkfield reflected low magnification.

FIG. 8 illustrates the use of darkfield reflected illumination at a particular angle of incidence, such that abundant platelets 84 are readily detected. The platelets 84 are small bodies that reflect brightly. They are readily distinguished from RBCs and WBCs, which are out of focus in this particular image. They are smaller by approximately 10 fold than RBCs and small lymphocytes and even more so compared to granulocytes.

Figure 9:
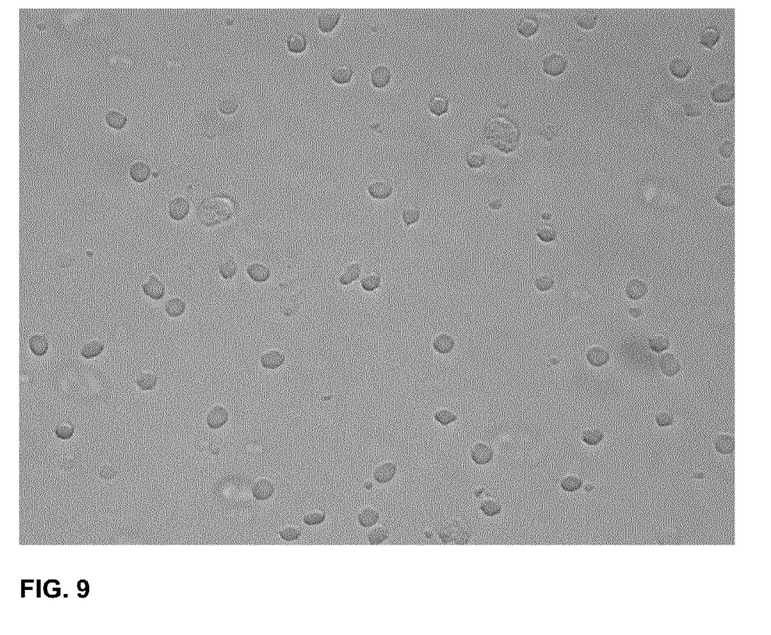
FIG. 9 is a photograph of a diluted sample with angled transmission and no stain.

In FIG. 9, an aliquot of blood, diluted with saline 1:20 (blood:saline) was place on a #0 coverslip and observed on an inverted microscope with transmitted illumination using white light, at a low angle to the plane of the coverslip. This angle of transmitted illumination provided a concave appearance to the cells. There is a clear distinction between red blood cells 80, white bloods cells 82 and platelets 84. A 50× objective was used. The RBCs can be readily examined for size and shape. The intensity of red coloration varies between specimens from different individuals under these conditions. This can be the basis for estimation of hemoglobin and subsequent determination of RBC characteristics conventionally reported in a CBC. The WBCs in this field include three granulocytes. The granules themselves show movement when viewed in real time.

Computing the Elements of a Complete Blood Count:

The images formed by the inverted microscope optics can be observed by a video camera (either color or black and white). The illumination source could be white light or one or more individual colors. The image from the video camera can be turned into a digital image. Multiple fields of view can be observed by moving the substrate. For example a motor controlled stage could move the substrate to observe a sufficient area of the drop to provide an analysis of sufficient numbers of each of the elements of the CBC. One or more images can be digitized from each field of view. For each image a single illumination mode, or a combination of modes can be applied while an image is digitized. One or more magnifications (i.e. objectives) can be used for each field of view. A single color, or multiple colors or white light can be applied while an image is digitized. Several images, using different illumination modes and colors (or in various combinations) could be digitized over time as the color or illumination mode is changed.

One mode of acquiring images would be transmitted angled illumination and reflected darkfield illumination, either separately, sequentially, or simultaneously depending upon the magnification, the volume and shape of the specimen drop, and the cell types or cell characteristics being analyzed. Using the resulting images, computer programs or human observers of the images can determine the elements of the CBC. Red blood cell and white blood cell counts can be determined. Platelet counts can be determined. The types of white blood cells can be determined. Other characteristics of the cells (such as hemoglobin content or granules in white blood cells) can be observed and analyzed.

Using these counts and cell characteristics, the following parameters could be determined:

Red Blood Cell (RBC) Parameters:
  a. RBC count by direct counting. The RBC count can be computed from an empirical relationship between the volume of blood in the drops and the cells in the layer;
  b. Mean corpuscular volume (MCV) can be determined by direct measurement of individual cells and calculation;
  c. Hematocrit (Hct) can be computed from MCV×RBC/1000;
  d. Hemoglobin (Hb) determined by reflectance or transmission spectroscopy or computed from formula Hb=MCH×RBC. The Hb of individual cells can be determined by reflectance spectroscopy of each of them following image processing that uses scene selection and object identification;
  e. Mean corpuscular hemoglobin (MCH) can be directly determined by making numerous measurements of Hb/RBC of individual cells, or by calculation;
  f. Mean corpuscular hemoglobin concentration (MCHC) from direct measurement of individual cells or by calculation of Hb/Hct; and
  g. RBC morphology; Image analysis (as in d) of individual RBCs followed by determination of size and shape can provide the customary morphological characterizations, such as, anisocytosis and poikilocytosis, etc.

White Blood Cells (WBC) Parameters:
  a. Cell count by direct counting; same principle applies as with RBC; and
  b. Differential count (enumerating different types of WBCs) by image analysis
  c. Recognition of abnormal WBC types.

Platelet Count by Direct Counting:

Same principle applies as with RBC, i.e. direct counting and the empirical relationship between the volume of the drop and the platelets in the layer.

From these basic parameter, several different embodiments are possible. Time is a factor in selecting a dilution. For example, a filed of view could be analyzed at a given time after a drop has been placed on the substrate, while using a lower dilution that would result in more than one cell layer forming. At a short time interval the cells would not yet be confluent, making the analysis easier. Knowing the time interval, the dilution, and the pattern of settling over time, total concentrations of the observed elements could be calculated.

In other embodiment multiple drops could be placed on a substrate. Each drop could have its own dilution; each drop could be stained or unstained, and each drop could be a different size.

In another embodiment, an aliquot could be lysed to eliminate the red blood cell elements. This would allow for the formation of a droplet of the substrate that would have a high density of white blood cells per unit area.

In another embodiment, a dilution factor could be chosen so that a droplet would never attain confluence after the elements settled on the substrate. Knowing the dilution and aliquot sizes, the most accurate possible calculation of the various elements of the blood sample could be calculated.

The foregoing description has been limited to a few embodiments of the invention. It will be apparent, however, that variations and modifications can be made to the invention, with the attainment of some or all of the advantages. Therefore, it is the object of the claims to cover all such variations and modifications as come within the true spirit and scope of the invention.

What is now claimed is:

1. A method of preparing and examining cells from a sample of blood, said method comprising the steps of:
  preparing the cells for examination by:
    placing an aliquot of whole blood on a surface of a transparent material, wherein the aliquot of whole blood comprises a distribution of cell types including red blood cells, white blood cells and platelets, and further wherein said aliquot of whole blood is placed on said surface of said transparent material without removing any of the cell types from the aliquot of whole blood; and
    allowing the cells to settle onto the surface of the transparent material for a period of between 10 seconds and two minutes to form a monolayer of cells; and
  examining from below the transparent material at least a portion of the monolayer to determine a count of a specific cell of the whole blood, wherein the examining comprises:
    directing illumination light to be incident on a surface of the transparent material at a first angle to the surface and obtaining a first image of the cells, wherein the first angle is selected to preferentially display a first subset of the cell types in the first image relative to the other cell types; and
    directing illumination light to be incident on a surface of the transparent material at a second angle to the surface and obtaining a second image of the cells, wherein the second angle is selected to preferentially display a second subset of the cell types in the second image relative to the other cell types,
    wherein the first and second subsets comprise at least one different type of cells.

2. The method of claim 1, wherein the aliquot is stained, diluted, or both.

3. The method of claim 1, wherein the aliquot is a stable droplet formed by a force selected from the group consisting of natural and external.

4. The method of claim 1, wherein the aliquot is examined with an inverted microscope.

5. The method of claim 1, wherein the illumination light is selected from the group consisting of white light, monochromatic light of one wavelength, monochromatic light of multiple wavelengths between the ultraviolet spectrum and the infrared spectrum, and polarized light.

6. The method of claim 1, wherein the inverted microscope has changeable lenses and wherein the changeable lenses are selected from the group consisting of low magnification, high magnification, deep depth of field, and shallow depth of field.

7. The method of claim 1, wherein the whole blood has a hemoglobin content, the method further comprising determining the hemoglobin content by measuring an absorption of a wavelength of the illumination light by the whole blood, and measuring a reflection of a wavelength of the illumination light by the whole blood.

8. The method of claim 1, further comprising using the count of a specific cell of the whole blood to calculate a parameter selected from the group consisting of hematocrit, hemoglobin, red blood cell count, assessment of red blood cell morphology, white blood cell differential count, and assessment of abnormal white blood cell morphology.

9. The method of claim 1, further comprising determining characteristics of the specific cell of the whole blood by a method selected from the group consisting of viewing the whole blood directly through a lens, viewing a digital image of the whole blood, and analyzing digital images of the whole blood automatically.

10. The method of claim 4, wherein the first and second images of the cells are obtained by detecting light from the cells, the detected light comprising at least a portion of the illumination light.

11. The method of claim 4, wherein the first and second images correspond to reflected darkfield illumination of the cells.

12. The method of claim 1, further comprising the step of assessing blood cell morphology with computer image analysis for automatically calculating a Complete Blood Cell Count and a White Blood Cell differential.

13. The method of claim 1, further comprising calculating at least one blood index selected from the group consisting of mean cell volume (MCV), mean cell hemoglobin (MCH), and mean cell hemoglobin concentration (MCHC).

14. The method of claim 1, wherein the aliquot is a representative portion of the whole blood.

15. The method of claim 1, wherein the first and second images are obtained by detecting illumination light reflected from the cells.

16. The method of claim 1, wherein the first and second images are obtained by detecting illumination light transmitted through the cells.

17. The method of claim 1, wherein the first image is obtained by detecting illumination light reflected from the cells, and wherein the second image is obtained by detecting illumination light transmitted through the cells.

18. The method of claim 1, wherein the first image is obtained by detecting light from the cells propagating along a direction perpendicular to the surface of the transparent material.

19. The method of claim 1, wherein the first angle is selected to preferentially display white blood cells in the first image.

20. The method of claim 1, wherein the first angle is selected to preferentially display red blood cells in the first image.

21. The method of claim 1, wherein the first angle is selected to preferentially display platelets in the first image.

22. The method of claim 19, wherein the second angle is selected to preferentially display red blood cells in the second image.

23. The method of claim 1, further comprising determining, for each of white blood cells and red blood cells in the sample, an illumination angle for preferentially displaying each cell type relative to other cell types in images of the sample.

24. The method of claim 23, further comprising determining, for each of white blood cells and red blood cells in the sample, an illumination wavelength for preferentially displaying each cell type relative to other cell types in images of the sample.

25. The method of claim 1, further comprising preparing the cells for examination by adding at least one of a dispersing agent and a colloidal agent to the cells to preferentially display the first subset of cell types in the first image.

* * * * *

UNITED STATES PATENT AND TRADEMARK OFFICE
CERTIFICATE OF CORRECTION

| | | |
|---|---|---|
| PATENT NO. | : 9,176,121 B2 | Page 1 of 1 |
| APPLICATION NO. | : 11/057095 | |
| DATED | : November 3, 2015 | |
| INVENTOR(S) | : James Winkelman et al. | |

It is certified that error appears in the above-identified patent and that said Letters Patent is hereby corrected as shown below:

IN THE CLAIMS

Column 11, Line 8, Claim 6, delete "claim 1," and insert -- claim 4, --.

Signed and Sealed this
Sixteenth Day of February, 2016

Michelle K. Lee
*Director of the United States Patent and Trademark Office*